(12) United States Patent
Golushko (10) Patent No.: US 7,216,039 B2
(45) Date of Patent: May 8, 2007

(54) METHOD AND DEVICE FOR CARRYING OUT CHROMATOGRAPHIC ANALYSES IN AN AUTOMATIC AND OPTIMISED MANNER

(75) Inventor: Sergey Golushko, Mühltal (DE)

(73) Assignee: VWR International, Inc., West Chester, PA (US)

( * ) Notice: Subject to any disclaimer, the term of this patent is extended or adjusted under 35 U.S.C. 154(b) by 402 days.

(21) Appl. No.: 10/480,593

(22) PCT Filed: May 31, 2002

(86) PCT No.: PCT/EP02/06014

§ 371 (c)(1),
(2), (4) Date: Dec. 12, 2003

(87) PCT Pub. No.: WO02/101384

PCT Pub. Date: Dec. 19, 2002

(65) Prior Publication Data

US 2004/0253147 A1    Dec. 16, 2004

(30) Foreign Application Priority Data

Jun. 13, 2001    (DE) ................................. 101 28 546

(51) Int. Cl.
*G06F 19/00* (2006.01)
(52) U.S. Cl. .......................................... 702/22; 702/23
(58) Field of Classification Search ............... 73/19.02, 73/23.22; 95/82; 702/22, 23
See application file for complete search history.

(56) References Cited

U.S. PATENT DOCUMENTS

| 5,305,232 A | | 4/1994 | Chimowitz et al. |
| 5,417,853 A | * | 5/1995 | Mizuno et al. ........... 210/198.2 |
| 5,738,707 A | | 4/1998 | Colombo et al. |
| 2002/0010566 A1 | | 1/2002 | Jianjun et al. |

FOREIGN PATENT DOCUMENTS

| DE | 19860354 A | 6/2000 |
| EP | 0783103 A | 7/1997 |
| WO | WO 0229401 A | 4/2002 |

* cited by examiner

*Primary Examiner*—John Barlow
*Assistant Examiner*—Douglas N Washburn
(74) *Attorney, Agent, or Firm*—Drinker Biddle & Reath LLP

(57) ABSTRACT

The invention relates to a method for automatically carrying out chromatographic analyses. According to said method, at least one of the following pieces of information is obtained: a) the retention times of at least one constituent; b) the temperature; c) the structural formulae of at least one of the constituents; d) the type of elution agent; and e) the parameters of the separation column. For extensive optimization, the invention is characterized in that the data obtained is optionally completed by available data, at least one first test run is carried out under isocratic conditions, and retention times are detected or calculated on the basis of a model with optimization parameters. The retention times obtained are optimized by varying the parameters, another chromatography run is carried out with the parameters of the optimized retention times, and a comparison is made with the measured retention times. The above-mentioned steps are optionally repeated for further optimization.

20 Claims, 4 Drawing Sheets

METHOD AND DEVICE FOR CARRYING OUT CHROMATOGRAPHIC ANALYSES IN AN AUTOMATIC AND OPTIMISED MANNER

The present invention relates to a method and a device for the automatic performance and optimization of chromatographic investigations with the help of an electronic data processing apparatus, the method having the following steps:
  i) Recording of data which include at least one of the following items of information
    a) Retention times of at least one component of the substance mixture, preferably for at least two different concentrations of an organic modifier,
    b) The temperature at which the retention times were ascertained,
    c) Structural formulae of components of the substance mixture,
    d) Type of eluent and concentration of an organic modifier therein,
    e) Parameters and/or sort and type of separation column.

The corresponding device has a chromatographic column or separation column, an inlet chamber for the substance mixture, an eluent feed, a measuring unit at the outlet of the chromatography column and also a data-recording unit for the automatic and/or manual inputting of data.

Corresponding methods and devices are known in the state of the art and are offered for sale and marketed for example by Merck KGaA under the name "LaChrom".

In principle, the known systems work reliably and quickly if the analytes, i.e. the individual components of the substance mixture, are adequately known. If it is for example a matter of confirming and/or excluding a specific composition of a substance mixture, such as e.g. of a drug, i.e. that e.g. a certain undesired by-product which can easily form in the preparation process is contained in the mixture, specific chromatography conditions can be set for this as standard on the basis of empirical values, and at least partly also allowed to proceed automatically. As the sought components, just like any undesired components, are known, the individual bands can be clearly allocated to the components using the chromatogram which was produced based on corresponding empirical values, quantitative estimates also being possible due to the surface area given below the bands.

The parameters to be modified are for example the temperature and the composition of the eluent. In the case of so-called "reversed-phase chromatography", which is the most important in practice, the eluent can be for example a mixture of water and a non-polar solvent, such as e.g. methanol or acetonitrile. The non-polar solvent is also called "organic modifier" in technical language. The so-called "stationary phase", i.e. the material contained in the chromatography column, is in general a highly porous solid or a packing of solid granules or particles, the surface of this solid phase likewise being non-polar and for this purpose optionally being coated with a non-polar material. The analytes accumulate on the surface of the solid phase and the through-washing and/or through-pressing of the eluent through the chromatography column has the result that within a certain period, a component is detached from the surface of the solid phase and discharged with the eluent at the outlet of the chromatography column. The time which elapses from the beginning of the chromatography run to the appearance of a component at the outlet of the chromatography column is called the "retention time" of this component. An essential parameter influencing the retention times in the chromatography column is the mixing ratio between water and organic modifier or, in other words, the concentration of the organic modifier in the eluent. Finally, as a further parameter, the material, i.e. the surface composition, and also the porosity and/or the grain size of the column material, play an important part.

The substance mixture introduced into an inlet chamber is firstly extensively adsorbed by the column material. The eluent then detaches, depending on the interaction with the individual components and their interaction with the column, the individual components from the column material and transports them gradually to the outlet of the chromatography column. Due to the different solubilities and interaction energies between the individual analytes and the eluent on the one hand and between the analytes and the column material on the other, the components are detached at different speeds in the eluent and inasmuch are also transported through and out of the column at different speeds. This leads to a separation of the individual components from one another which are transported consecutively out of the outlet of the column and through the measuring cell. If the solubilities at a given concentration are very different, this bears on the duration of the chromatography run, because the portion of better-soluble components possibly appears relatively quickly at the outlet of the column whereas very poorly-soluble components take an extremely long time until they have been detached by the eluent and transported to the outlet of the column. In this case, the chromatogram, which is e.g. nothing other than the UV absorption in the cell as a function of time, can be very prolonged and thus require a very great deal of time, in addition to which the bands or peaks which appear very late can also be markedly flattened and thus scarcely recognizable.

This is encountered in general by increasing the concentration of the so-called organic modifier. Increasing the concentration of the organic modifier increases the probability of the components of the substance mixture being separated from the chromatography column and transported by the eluent. However, this can also result in different components appearing almost simultaneously at the outlet of the chromatography column, so that the corresponding bands can no longer be clearly separated from one another and in particular the surface below the bands can also no longer be sufficiently precisely recorded.

While the correct parameters can be set without major problems in the case of routine chromatography runs with which for example merely a consistent quality of a specific product is to be ensured, the setting of the parameters in the case of substance mixtures whose composition is not, or only partly, known represents a considerable problem. With known substances or routine investigations, the optimum parameters are selected on the basis of empirical values, i.e. essentially the column material, the temperature to be set and the concentration of the organic modifier.

Parameters are regarded as "optimum" which result in each component of the substance mixture being individually recognizable as separate bands clearly separated from the bands produced by other components on the chromatogram, and furthermore the time required overall for a chromatography run is as short as possible.

The "ideal" chromatogram consequently consists of a series of bands in close succession which are also fully separated from one another, where the first band should appear as early as possible after the start of the chromatography run. The "bands" or "peaks" can be produced for example by UV absorption, the eluent leaving the chromatography column being guided, together with the material dissolved therein, through a measuring cell which is irradiated from one side with UV light, while on the opposite side of the cell there is arranged a detector for UV light with the help of which the UV absorption of the components, which are contained in the eluent flowing though the cell, of the substance mixture can be recorded. Naturally other detection methods for the individual, dissolved components are also conceivable, including mass-spectrometry investigations.

In order to avoid both too long a duration for the chromatogram and a defective band separation, in many cases the concentration of the organic modifier is varied during the chromatography run (so-called gradient elution chromatography). At the start there is generally a low concentration of organic modifier, which is e.g. increased continuously until the end of the chromatography run. It is however often expedient not to leave the concentration gradient constant, but vary it more markedly and e.g. to change the concentration in stages or also to only change it continuously for a limited time and otherwise to proceed at constant concentrations.

Because in addition the temperature is also available as a variation parameter, the control of chromatography runs becomes increasingly more complicated the more components are contained in a substance mixture and the less that is known about the substance mixture. With largely unknown substance mixtures, frequently expensive and lengthy test runs are required, the user of such a chromatography apparatus deciding, on the basis of intermediate results and on the basis of possibly many years' experience which parameters are to be changed and when. This is not only a very time-consuming process which simultaneously also requires a very great amount of manpower, but is moreover also a procedure which is very prone to errors, as the changing, based on intuition and experience, of parameters, which is often carried out in order to limit the long duration of a chromatography run and to accelerate the process, very often results in bands coinciding unnoticed so that certain components are not identified or found at all.

In the state of the art the method has thus far been automated inasmuch as the user of the chromatography apparatus selects and inputs a set of parameters and the chromatography apparatus then automatically carries out the chromatography runs with the selected parameters. For this, very many test runs are usually necessary and not all the selected parameters lead to meaningful results. The best results must be read manually from the obtained chromatograms.

Compared with this state of the art, the object of the present invention is to create a method and a device for chromatography investigations which require less manpower and yet can ensure a full recording of all components, or as many components as possible, of the substance mixture in a relatively short time.

This object is achieved by a method according to claim 1 and a device according to claim 16.

The method according to the invention proposes in general the following steps:
i) Recording of data which include at least one of the following items of information
   a) Retention times of at least one component of the substance mixture, preferably for at least two different concentrations of an organic modifier,
   b) The temperature at which the retention times were ascertained,
   c) Structural formulae of one or more of the components of the analyte,
   d) Type of eluent and also the concentration of an organic modifier therein,
   e) Parameters or type of separation column, the recorded data being fully or partly able to also be retrieved and/or supplemented from a data storage apparatus and, where data are unavailable for the items of information according to a), b) or c), at least a first test run taking place under isocratic conditions in order to record retention times according to a), and preferably a further isocratic test run being carried out with a different concentration of the organic modifier,
   ii) Calculation of retention times as a function of settable parameters based on a model which reproduces a functional relationship of at least part of the data recorded under i), the recorded data also being able to be reproduced by setting model parameters,
   iii) Optimization of the retention times in the model by varying the concentration of the organic modifier and/or of the temperature,
   iv) Carrying out at least one further chromatography run with the parameters of the retention times optimized according to step iii), and comparing the actual retention times with the theoretically calculated, optimized retention times,
   v) Optionally single or repeated repetition of steps i) to iv) if the deviations of the calculated and the measured retention times exceed a presettable limit value or if the differences between the retention times of two successive chromatography runs fall short of a presettable limit value,
      all above-named steps, with the exception of an initial data input, proceeding automatically and independently under the control of a data processing apparatus with an artificial intelligence module.

It is known to a person skilled in the art that retention times can also be influenced by other parameters such as e.g. pH value or ionic strength. According to the invention, these parameters are collectively called optimizing parameters. If the substance mixture consists only of a few components, the retention times of which at specific concentrations of the organic modifier are known, it is in general relatively simple to set the concentration, the concentration pattern and/or the temperature such that each of the components has a clearly distinct retention time with the result that the corresponding peaks of the chromatogram are cleanly separated from one another and yet simultaneously the longest retention time of the components is kept as short as possible.

If however the number of components is relatively large and the retention times have different, in some cases clearly distinct, concentration and/or temperature relationships, the whole system very quickly becomes difficult to oversee and can be optimized only with luck even with a great deal of experience by decisions of the user. According to the present invention, it is proposed for this case to carry out an optimization with the help of mathematical procedures by choosing the retention times as functions of the settable variables in a model, i.e. based on a model which contains at least part of the available data as parameters or measured values. By varying the concentration of the organic modifier and/or of also the temperature in the model, the retention times are subsequently optimized, it being understood that the retention times actually measured at given concentrations must be reproduced correctly in the model. This is done in general by adapting model parameters which are assumed to be constant for further optimization. An artificial intelligence module ultimately decides which parameters are regarded as optimum and sends corresponding instructions to a control unit.

The more difficult application of the method according to the invention occurs if only a few components of the substance mixture are known, but the majority are not known. For these components, either specific retention times at certain concentrations of the organic modifier can be known or alternatively or in addition the structural formulae of components of the substance mixture. Based on these data, a theoretical model is again taken as a basis and with this theoretical model the retention times of all the known components at various concentrations are calculated and the concentrations of the organic modifier optimized as a function of time. The temperature can also be used as an additional optimizing parameter, in particular e.g. if two components are difficult to separate from one another at a given temperature, yet at the same time their retention times display a clearly distinct temperature pattern.

If no data whatsoever are available regarding structural formulae or retention times, a test run is simply carried out under isocratic conditions, i.e. at a constant concentration of the organic modifier.

Preferably a second test run is also carried out at a second concentration of the organic modifier. Usually at least some bands appear at both concentrations in the respective chromatogram. Starting from the time of the introduction of a substance mixture into a suitable inlet chamber and the inputting of the optionally previously available data, the process runs fully automatically and the corresponding device is designed for such an automatic process, i.e. in addition to the basic constituents of a chromatography column with inlet chamber for the substance mixture, an eluent feed and the measuring unit at the outlet of the chromatography column, it also has a data-recording apparatus for the automatic and/or manual inputting of data, an associated optimization unit which calculates, based on the most recently recorded data of a system, optimized parameters for a (further) chromatography run and a control apparatus and also parameter sensors which are provided to automatically set the parameters ascertained in the optimization unit and to control the parameters according to the automatically ascertained process.

If two test runs have been carried out, it can be attempted to assign measured bands of the two chromatograms to each other or to a specific component. A clear assignment is achieved by using standards for each individual component of the substance mixture and carrying out the experiments only with the respective individual standards. Standards of the individual components with a purity >80% are preferably used for this. The method can be further improved by using intelligent peak-tracking strategies. In the preferred version, a suitable model expediently assumes that the retention times decrease with increasing concentration of the organic modifier. The surface present below a band of the chromatogram offers further assistance. This naturally assumes that identical quantities of the substance mixture are introduced into the chromatography column each time or that at least the introduced quantities are precisely known and the substance mixture has a constant composition. An assignment of the peaks can also be carried out via spectral properties of the components. As a result of these peak-tracking strategies, the number of standards required can be reduced to two and the optimizing experiments carried out both firstly with the standards and also thereafter with the substance mixture.

The optimization unit then again calculates, on the basis of the recorded concentration pattern of the retention times for the different components of the system, optimized parameters which are set in a further chromatography run. The retention times actually measured are compared with the previously calculated times and the model parameters taken as a basis are adapted such that the model now reproduces the retention times actually measured. Based on the thus-adapted model "constants", optimized parameters of the chromatography run (concentration pattern and/or temperature) can be calculated and set once again. The optimized parameters calculated each time, the retention times calculated therefrom and also the retention times then measured with the same set parameters are automatically recorded in a data-recording apparatus and stored arranged such that a substance mixture can clearly be allocated the corresponding iterative sequence of chromatography runs, the set parameters and the measured values. The end of such a series is a chromatography run with optimized parameters, the criterion chosen for definitively optimized parameters being e.g. the condition that a maximum number of bands or peaks is recorded separately and a preset time limit is not exceeded, the time limit also being able to be a time dependent on the number of recorded peaks. The data storage can, if necessary, also be limited to the last set of optimized parameters for a given substance mixture.

A further optimizing criterion chosen can be the condition that the changes in the retention times and/or parameters, which have been obtained on the basis of two or more iterative chromatography runs differ only slightly from one another, so that it is to be expected that even further iterative optimizations will deliver only slight improvements.

The method according to the invention can run fully automatically with the exception of an initial inputting of known data, such as e.g. the known structural formulae of components of the substance mixture, the separation column type and any already-known retention times. As already mentioned, the essentially settable parameters are the concentration of the organic modifier and the temperature.

If only a few components of the substance mixture are available as standards, the retention times for the remaining components are calculated and/or optimized in the model taken as a basis on the condition that the parameter space covered by the components present as standards is not exceeded. Such a parameter space contains e.g. restrictions in respect of the possible concentration of an organic modifier because in every case the components (at least two) must be recorded within a preset time limit. Parameter conditions with which the two known components would not be clearly separable from one another are also to be excluded. The parameters to be set then need still be sought only in the remaining range. The situation is analogous, of course, if more than two components are available as standards.

When carrying out the test runs and also during further chromatography runs in the course of the iterations, the number of peaks or bands of the chromatogram that are measured overall is also recorded. Starting from an ascertained maximum number of peaks, the parameters are further changed for optimization only inasmuch as the number of recorded peaks does not fall as a result. This also necessitates considerable restrictions of the available parameter space and thus a clear acceleration of the optimization.

To calculate and optimize the retention times, a so-called peak-tracking strategy is preferably used which is based on the identification of peaks in a two-dimensional graph in which the retention times belonging to the peaks are represented as a function of the concentration of the organic modifier. It is understood that this does not require a specific two-dimensional representation, but that such a graph can also be purely mathematically abstractly recorded and analyzed. In the process, the condition is used, among others, that two peaks which have been recorded with different parameters are regarded as belonging to the same component only if the retention time or the natural logarithm of the retention time is a function that decreases as the concentration of the organic modifier increases.

A further criterion for the identity of peaks is the similarity of the surfaces contained below a peak. Accordingly, two peaks are regarded as not identical or not belonging to the same component if the relative differences in the peak surfaces exceed a preset limit value at a given change in concentration of the organic modifier. Moreover, two peaks can be regarded as identical if the spectral properties of the components producing these peaks are identical or very similar. Accordingly, two peaks are regarded as not identical or not belonging to the same component if the differences in the spectral properties exceed a preset limit value.

The method can be improved by also calculating the retention times for at least one alternative stationary phase, i.e. an alternative column material and optimizing them in relation to the variable parameters. This is expedient particularly if a satisfactory result cannot be achieved for the initially considered column material, i.e. either disproportionately long retention times must be accepted or else not all the components of the substance mixture are recorded. In this case, another eluent can also be considered and a change made to a different chromatography column with the same or a different eluent. The model parameters ascertained based on the first column material and the first organic modifier or eluent can with certain restrictions be transferred to the model parameters for the new column material and the new eluent or converted. The optimizing times can thereby likewise be considerably shortened for the second column material and/or the second eluent. Expediently therefore, such transfers to different chromatography columns or different eluents initially take place theoretically only on the basis of the discussed model and a change then preferably takes place only if the optimizations carried out on this theoretical basis promise a clear improvement vis-à-vis the initially used chromatography columns or eluents. With the method according to the invention, the parameters, i.e. concentration of the organic modifier as a function of time or the temperature, are automatically set during the various chromatography runs which are optionally to be carried out in the course of the optimization. A user need therefore only monitor the system or a corresponding chromatography system at certain intervals, the stored data expediently being recorded in the form of protocols and being shown on a screen or also another reproduction medium.

An artificial intelligence module is expediently used to decide on chromatography runs and the parameters to be set, which is e.g. capable of reaching compromises between the peak separation and the overall duration. Such an artificial intelligence module can also be used for the optimization. In the search for optimum parameters for example, a so-called Monte Carlo optimization can also be carried out.

The calculation of the retention times is carried out, depending on whether certain data are known, according to different models. One model, which is also called a solvatic model, is defined by the equation $\ln k' = a(V^{2/3}) + b(\Delta G) + c$, $k'$ being the so-called capacity factor which corresponds to a retention time adjusted by the dead time, $V$ being the volume of the molecule of a sought component, $\Delta G$ the interaction energy of the molecule with water, and $a$, $b$ and $c$ parameters of the sorbent/eluent system. While $a$, $b$ and $c$ are obtained by calibrations of sorbent/eluent systems, $V$ and $\Delta G$ are adjusted in the course of the optimizing process using the measured values. In addition, an empirical model for the retention times can also be used simply by adaptation using polynomials according to the equation $\ln k' = a + bx + cx^2 + \ldots$, $k'$ again being the previously mentioned capacity factor and $x$ being defined as follows, depending on the chromatography method:

| | |
|---|---|
| Reversed-phase chromatography | $x = C$ |
| Normal-phase chromatography | $x = \ln(C)$ |
| Ion-exchange chromatography | $x = \ln(C)$ |
| pH value of a buffer | $x = pH$ |
| Temperature | $x = 1/T$ |

(C = concentration)

The coefficients $a$, $b$ and $c$ are model parameters which are to be set such that the known or measured values are correctly reproduced. Naturally, both models can also be applied combined with each other or independently of one another to a given system, the solvatic model naturally being able to be used only if individual components or their structural formulae or molecule parameters are known. The mentioned method is further improved if an artificial intelligence module is used which, on the basis of the results of the preceding experiments, allows the parameters for the next experiment to be set.

It is also assumed, without further statements, that a person skilled in the art can use the above description to the broadest extent. The preferred versions and examples are therefore to be understood merely as a descriptive, but in no way limiting, disclosure.

The full disclosure of all applications, patents and publications listed previously and hereafter, and also the corresponding application DE 101 28 546.9 are incorporated into this application by reference.

Further advantages, features and possible applications of the present invention follow from the following representation of an embodiment.

In principle, there are several different starting conditions. One initial situation is e.g. characterized in that the structural formulae of at least some of the components are known. Retention times for a specific column type and an organic solvent can then be estimated in accordance with the solvatic model. There follows a test run with correspondingly set conditions.

According to another scenario, no structural formulae whatsoever are known for components and the substance mixture is essentially unknown. Here, a test can initially be carried out with a typical column material and a typical organic solvent. If this test is not successful, different column types and organic solvents are tried out, initially under isocratic conditions, i.e. in each case with a fixed concentration of an organic solvent, which concentration should not be chosen too low, and in addition two test runs should preferably be carried out, each with a clearly distinct concentration of the organic modifier.

Figure 1:
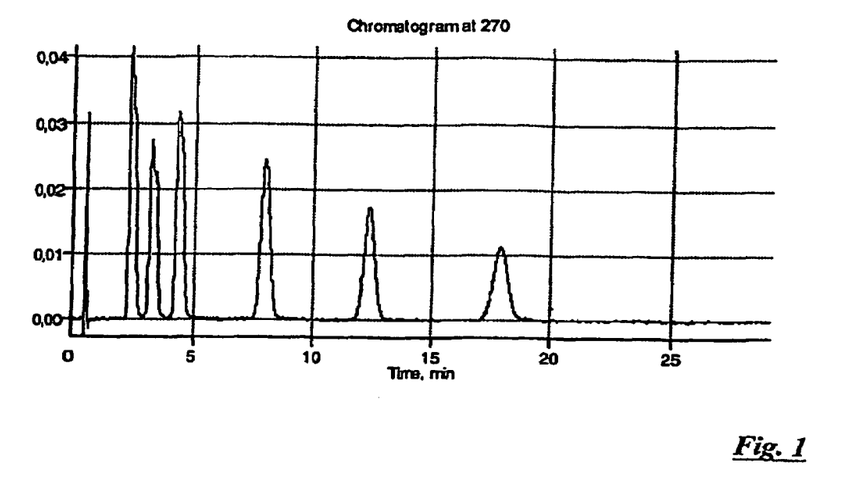
Figure 2:
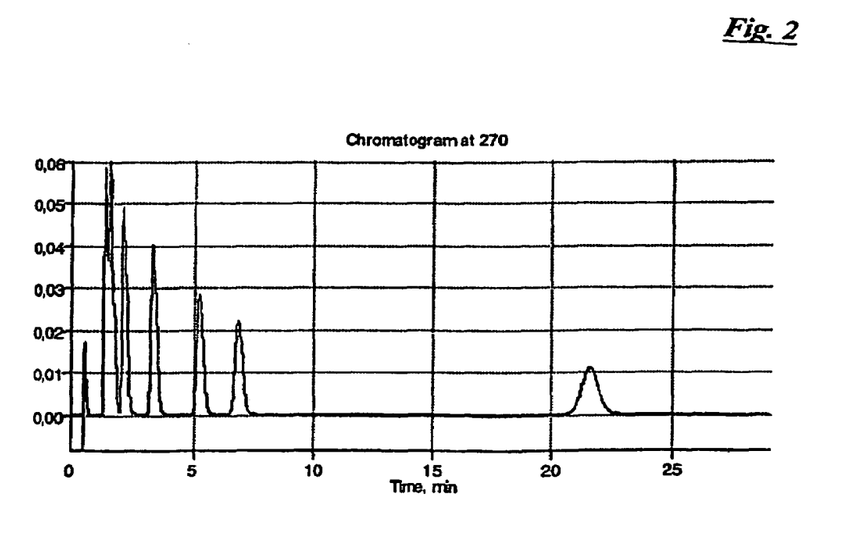

FIG. 1 shows by way of example a chromatogram as was ascertained for seven sulphonamides under isocratic conditions at a first concentration of an organic modifier. However only 6 peaks are clearly distinguishable. FIG. 2 shows the results for the same system, but with a second, lower concentration of an organic modifier. Here also only 6 peaks are clearly recognizable. The double structure of the first peak in FIG. 2 and also the irregularities in the second peak in FIG. 1 indicate however that at least one further analyte, which has not yet been dissolved in this chromatogram, is hidden in the substance mixture.

If structural formulae are known, the solvatic retention model is taken as a specific basis. If the structures are known, the system calculates the values for V and for ΔG automatically according to known methods (1. S. V. Galushko, J. of Chromatography, 552 (1991), 91–102; 2. S. V. Galushko, A. A. Kamenchuk, G. L. Pit, J. of Chromatography A, 660 (1994) 47–59). The parameters a, b and c which are determined by the solvent or the eluent and the stationary phase are obtained by a calibration with a known standard system from substance mixtures or individual components. For further calculation, the parameters a, b and c then remain unchanged, so that the retention times result directly from the structural formulae. Due to the concentration dependency of the parameters a, b and c, the optimum concentrations for a substance mixture comprising several components can now also be calculated if all the components are to be recorded separately from one another within a reasonable time.

A test run is then carried out with the correspondingly calculated parameters. The test results are then used for the refinement of the model parameters and a new calculation of retention times until the model agrees with the times measured in reality. The then-optimized molecule parameters V and ΔG and also the set parameters for an optimum chromatography run are then stored for future use.

If the structures are not known, the empirical model is used. A first run is initially carried out under isocratic conditions. Then a second run is carried out with a different concentration of organic modifier, the second concentration being chosen either clearly higher or clearly lower depending on the results of the first run. After the second run has also been carried out and the data are recorded, if a linear model is used initially, i.e. in the polynomial mentioned above $\ln k'=a+bx+cx^2+\ldots$ only the coefficients a and b are assumed to be other than 0.

Optimized conditions are calculated anew from this and a further test run carried out. On the basis of the three measured values then available in total, the quadratic model can be used, i.e. the parameter c is now also assumed to be other than 0. A further optimization takes place starting from that previously ascertained; optimum isocratic concentrations by ascertaining an optimum gradient profile. The system can produce a large number of corresponding gradient profiles according to the random principle and in each case calculate, with the previously ascertained, optimized model parameters, the associated chromatogram or the position of the bands of the individual components, wherein a suitable optimization criterion (e.g. the product of the intervals between all the adjacent peaks divided by the square of the longest retention time) is to be selected and the optimum profile can then be ascertained, using so-called "Monte Carlo methods", according to the random principle. Additional boundary conditions such as e.g. the condition that the concentration can only be constant or increasing, facilitate the discovery of an optimum gradient profile.

As a result at least part of the following data is obtained in the course of an optimization:

1) Optimum isocratic conditions,
2) Optimum conditions with linear gradient,
3) Different gradient profiles with gradient varying stepwise based on the different retention models.

It transpires that the optimum conditions are very often at times isocratic conditions, the transfer from an initially low concentration to a higher concentration taking place with a very steep gradient and almost sharply.

The time required for an optimization naturally depends on the number of components or compounds to be analyzed. 10–12 hours are usually required to optimize the conditions for a substance mixture with five components on a conventional column. If the molecule parameters V and ΔG are known, the optimization can take place even more quickly. The method according to the invention and the corresponding device have above all the advantage that they proceed automatically without external measures by operators as soon as a few parameters have been inputted and the system has been started.

An embodiment is represented below which shows the automated optimization of a chromatography of seven sulphonamides using only two standards. The two standards were sulfathiazole and sulfameracil. Purospher STAR RP18e was used as sorbent, 0.005 m phosphate buffer pH=3.5 as eluent.

Detection at 270 nm
Temperature 30° C.
Flow rate 1.0 ml/min
Injection volume 10 μl
Dead time at 0.4 minutes
Washing time on new solvent 6.0 minutes
Starting concentration 80%
Delay time 1.25 minutes.

Nine successive test runs were carried out for sulfathiazole and sulfameracil under these test conditions, the concentration of the eluent being reduced from run to run, starting from 80% through 60, 40, 25, 19, 13, 8 to 6%, a further run being carried out at 12%. Each time, the time until the passage of a peak was measured and in each case the peak resolution factors and the factor $K'_{max}$ measured, i.e. the maximum standardized duration (T–TO)/TO with T=retention time and TO=dead time.

Both peaks were found down to concentration of 8% in each case, the resolution factor RS improving continuously from 0.08 through 0.19, 0.82, 0.96, 1.62, 2.46 to 3.82. A further reduction of the concentration to 6% resulted in the peak for sulfathiazole not being found. An increase in the concentration compared with the previous 8% led to a slight reduction of the resolution factor and to a lowering of the maximum standardized retention time $k'_{max}$.

Accordingly the best isocratic conditions had been measured at a concentration of 8%. Thereafter runs were carried out with the whole mixture. An elimination criterion was a peak surface of 30,000 in unit areas (e.g. μVs). In 18 runs, the concentration was reduced step-wise from 80% through 71%, 63%, 55%, 49%, 45%, 35%, 28%, 25%, 22%, 19%, 16%, 13%, 10%, 7%, 5% and raised again to 8% and 12%. The retention times, the peak widths, the peak surfaces and the number of theoretical plates of the peaks were ascertained. Likewise the pair resolution and also the standardized retention time were also ascertained from the chromatograms. It transpired that an isocratic concentration of 19% delivered the best values.

Only then are e.g. linear retention models built up, taking into account e.g. the surface, the retention time and spectral data of the peaks.

Elution with an 80-% concentration for approximately 250 seconds is always carried out between each of the runs.

Figure 3:
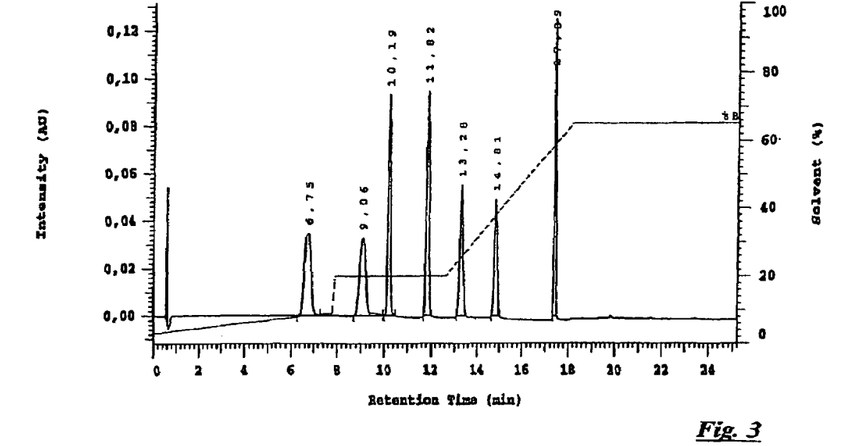
Figure 4:
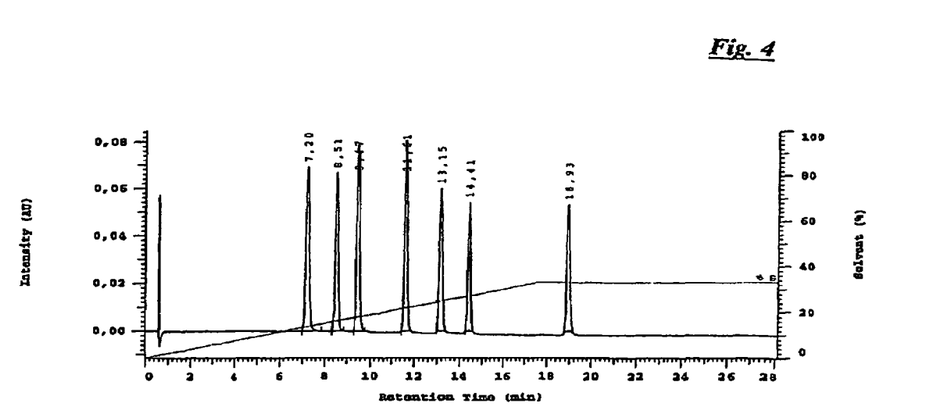
Figure 5:
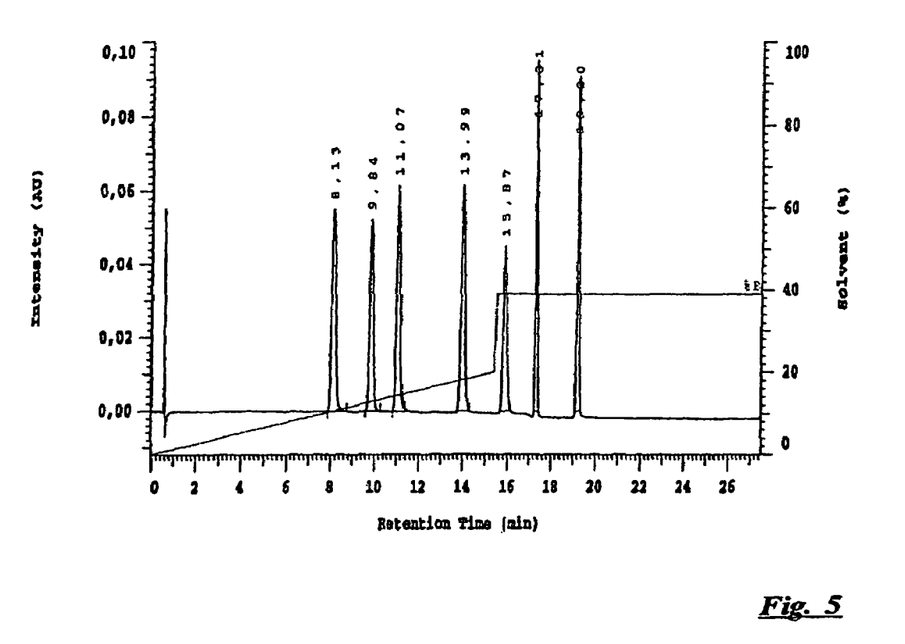
Figure 6:
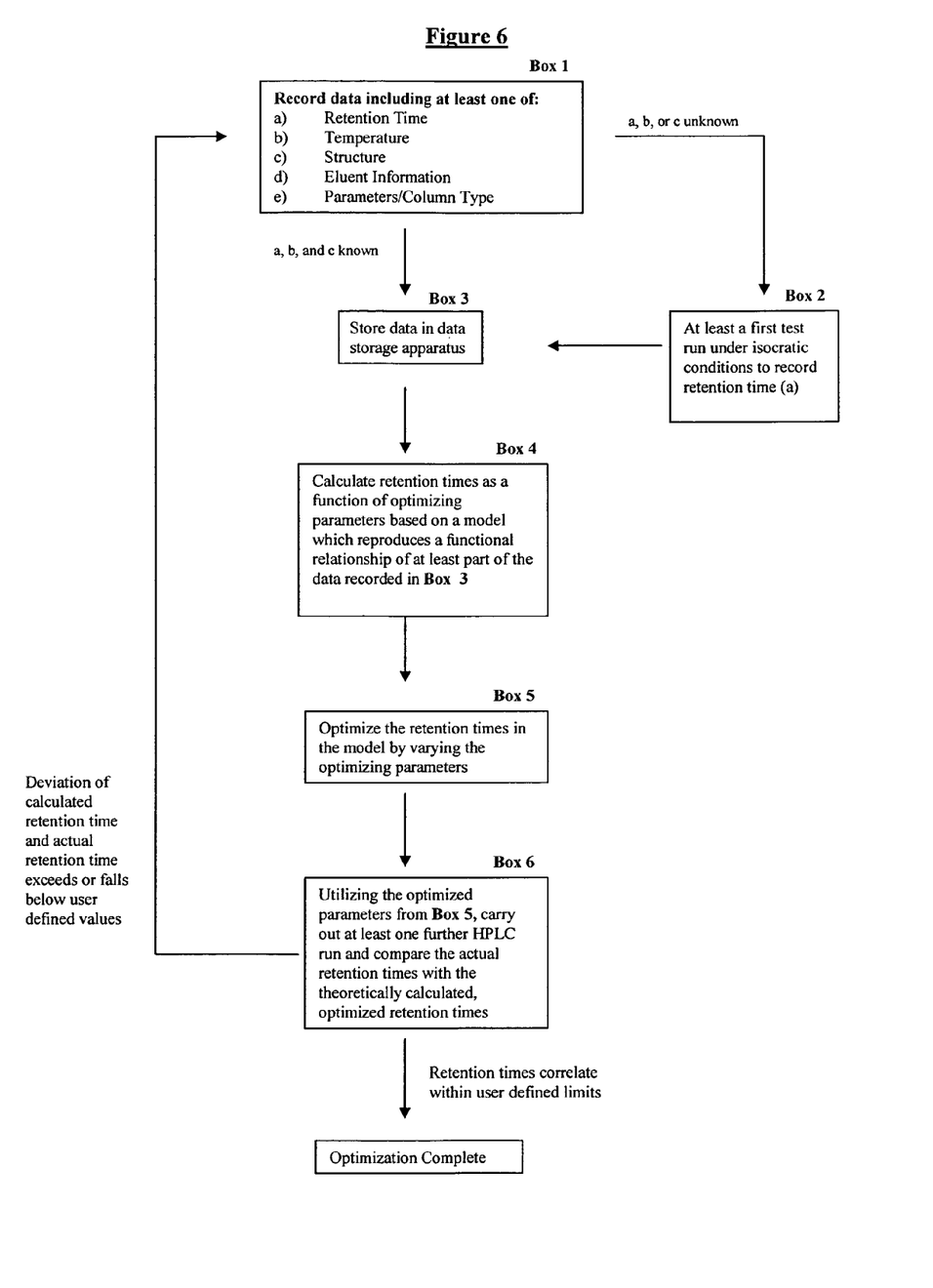

Two of the chromatograms which resulted from the aforementioned tests are shown in the already discussed FIGS. 1 and 2, FIG. 2 showing the optimum for isocratic conditions. The system them modifies the test runs by setting gradients of the eluent. For this for example a linear retention model is built up which takes into account the measured retention times, the peak surfaces and the spectral data. On this basis, multi-stage gradients are sought and used in further runs. Examples of this are shown in FIGS. 3, 4 and 5.

It is essential that the chromatography conditions are chosen such that all seven peaks which were found in previous tests are obtained in every case, appear within an acceptable time and are easily separable from one another and able to be resolved. An essential criterion is therefore, in addition to the number of peaks, the parameter of pair resolution. For the gradient pattern shown in FIG. 3, in addition to the clearly recognizable seven peaks, a parameter of pair resolution of 3.511 is obtained for the critical peak pair and a maximum retention time of approximately 17.5 minutes. In the case of the gradient pattern according to FIG. 4, a maximum retention time of just 19 minutes, but also an improved parameter of pair resolution of 4.341, results. A further improved pair resolution with a value of 4.506 is obtained for the gradient pattern as finally represented in FIG. 5. The ascertained maximum retention time of 19.2 minutes is in every case still in an acceptable range with the result that the chromatography conditions represented in FIG. 5 (gradient pattern) in the present example were selected as optimum after further test runs yielded no better pair resolution and at most a slight reduction of the maximum retention time.

The invention claimed is:

1. Method for the automatic performance of chromatographic investigations with the help of an electronic data processing apparatus and comprising the steps of:
  i) Recording of data which include at least one of the following items of information
    a) Retention times of at least one component of the substance mixture, preferably for at least two different concentrations of an organic modifier,
    b) The temperature at which the retention times were ascertained,
    c) Structural formulae of one or more of the components of the substance mixture,
    d) Types of eluent and also the concentration of an organic modifier therein,
    e) Parameters or type of separation column, the recorded data being fully or partly able to be retrieved and/or supplemented from a data storage apparatus and, where data are unavailable for the items of information according to a), b) or c), at least a first test run taking place under isocratic conditions in order to record retention times according to a), and preferably a further isocratic test run being carried out with a different concentration of the organic modifier,
  ii) Calculation of retention times as a function of optimizing parameters based on a model which reproduces a functional relationship of at least part of the data recorded under i), the recorded data also being able to be reproduced by setting model parameters,
  iii) Optimization of the retention times in the model by varying the optimizing parameters.
  iv) Carrying out at least one further chromatography run with the parameters of the retention times optimized according to step iii), and comparing the actual retention times with the theoretically calculated, optimized retention times,
  v) Optionally single or repeated repetition of steps i) to iv) if the deviations of the calculated and the measured retention times exceed a presettable limit value or if the differences between the retention times of two successive chromatography runs fall short of a presettable limit value,
  the decision for parameters to be specifically set for a next run preferably being taken by an artificial intelligence module.

2. Method according to claim 1, wherein on the basis of the manually inputted initial data such as e.g. the structural formulae of components of the substance mixture, the separation column type and already known retention times and parameters, steps i) to v) proceed automatically, with the exception of an initial inputting of data.

3. Method according to claim 1, wherein the ascertained optimized values preferably including the values ascertained in intermediate steps, are stored in a database.

4. Method according to claim 1, wherein before step ii) the recorded data are compared with stored data.

5. Method for the automatic performance of chromatographic investigations with the help of an electronic data processing apparatus and comprising the steps of:
  i) recording of data which include at least one of the following items of information:
    a) retention times of at least one component of the substance mixture, preferably for at least two different concentrations of an organic modifier,
    b) the temperature at which the retention times were ascertained,
    c) structural formulae of one or more of the components of the substance mixture,
    d) types of eluent and also the concentration of an organic modifier therein,
    e) parameters or type of separation column, the recorded data being fully or partly able to be retrieved and/or supplemented from a data storage apparatus and, where data are unavailable for the items of information according to a), b) or c), at least a first test run taking place under isocratic conditions in order to record retention times according to a), and preferably a further isocratic test run being carried out with a different concentration of the organic modifier,
  ii) calculation of retention times as a function of optimizing parameters based on a model which reproduces a functional relationship of at least part of the data recorded under i), the recorded data also being able to be reproduced by setting model parameters,
  iii) optimization of the retention times in the model by varying the optimizing parameters.
  iv) carrying out at least one further chromatography run with the parameters of the retention times optimized according to step iii), and comparing the actual retention times with the theoretically calculated, optimized retention times,
  v) optionally single or repeated repetition of steps i) to iv) if the deviations of the calculated and the measured retention times exceed a presettable limit value or if the differences between the retention times of two successive chromatography runs fall short of a presettable limit value,
  the decision for parameters to be specifically set for a next run preferably being taken by an artificial intelligence module, and wherein the concentration of the organic modifier, the pH value and the temperature T are used as optimizing parameters.

6. Method according to claim 1, further comprising the step of:

Fixing of a maximally available parameter space by test runs with at least two standards using the condition that the standards can be detected separately from one another within a presentable maximum time.

7. Method for the automatic performance of chromatographic investigations with the help of an electronic data processing apparatus and comprising the steps of:
   i) recording of data which include at least one of the following items of information:
      a) retention times of at least one component of the substance mixture, preferably for at least two different concentrations of an organic modifier,
      b) the temperature at which the retention times were ascertained,
      c) structural formulae of one or more of the components of the substance mixture,
      d) types of eluent and also the concentration of an organic modifier therein,
      e) parameters or type of separation column, the recorded data being fully or partly able to be retrieved and/or supplemented from a data storage apparatus and, where data are unavailable for the items of information according to a), b) or c), at least a first test run taking place under isocratic conditions in order to record retention times according to a), and preferably a further isocratic test run being carried out with a different concentration of the organic modifier,
   ii) calculation of retention times as a function of optimizing parameters based on a model which reproduces a functional relationship of at least part of the data recorded under i), the recorded data also being able to be reproduced by setting model parameters,
   iii) optimization of the retention times in the model by varying the optimizing parameters,
   iv) carrying out at least one further chromatography run with the parameters of the retention times optimized according to step iii), and comparing the actual retention times with the theoretically calculated, optimized retention times,
   v) optionally single or repeated repetition of steps i) to iv) if the deviations of the calculated and the measured retention times exceed a presettable limit value or if the differences between the retention times of two successive chromatography runs fall short of a presettable limit value,
   the decision for parameters to be specifically set for a next run preferably being taken by an artificial intelligence module, and wherein a maximum number of peaks being used additionally as an optimization criterion in step iii).

8. Method for the automatic performance of chromatographic investigations with the help of an electronic data processing apparatus and comprising the steps of:
   i) recording of data which include at least one of the following items of information:
      a) retention times of at least one component of the substance mixture, preferably for at least two different concentrations of an organic modifier,
      b) the temperature at which the retention times were ascertained,
      c) structural formulae of one or more of the components of the substance mixture,
      d) types of eluent and also the concentration of an organic modifier therein,
      e) parameters or type of separation column, the recorded data being fully or partly able to be retrieved and/or supplemented from a data storage apparatus and, where data are unavailable for the items of information according to a), b) or c), at least a first test run taking place under isocratic conditions in order to record retention times according to a), and preferably a further isocratic test run being carried out with a different concentration of the organic modifier,
   ii) calculation of retention times as a function of optimizing parameters based on a model which reproduces a functional relationship of at least part of the data recorded under i), the recorded data also being able to be reproduced by setting model parameters,
   iii) optimization of the retention times in the model by varying the optimizing parameters.
   iv) carrying out at least one further chromatography run with the parameters of the retention times optimized according to step iii), and comparing the actual retention times with the theoretically calculated, optimized retention times,
   v) optionally single or repeated repetition of steps i) to iv) if the deviations of the calculated and the measured retention times exceed a presettable limit value or if the differences between the retention times of two successive chromatography runs fall short of a presettable limit value,
   the decision for parameters to be specifically set for a next run preferably being taken by an artificial intelligence module, and wherein to calculate and optimize the retention times, a peak-tracking strategy is used which is based on the identification of peaks in a two-dimensional graph in which the retention times belonging to the peaks are represented compared with the optimizing parameters.

9. Method according to claim 8, wherein peaks are allocated to one another as identical only if, for their connecting line in the two-dimensional representation retention time vs concentration of the organic modifier, the following is true: $d\ln T/dC < 0$, C being the concentration of the organic modifier.

10. Method according to claim 8, wherein peaks are regarded as not identical if the relative deviations of the peak surfaces of a seemingly identical component exceed a preset limit value.

11. Method according to claim 8, wherein peaks are not regarded as identical if deviations of spectral parameters exceed a preset limit value.

12. Method according to claim 1, which furthermore includes the step that the retention times are calculated and/or optimized in relation to the variable parameters for at least one alternative stationary phase (alternative column material).

13. Method according to claim 12, wherein an automatic change to a different column and/or a different eluent takes place if the model predicts that the optimization criteria will be better fulfilled thereby than with the first column material and/or eluent.

14. Method according to claim 1, wherein preset data and parameters and also the associated retention times, the number of peaks and the peak surfaces for all test runs and optimized chromatography runs are stored assigned to one another if they relate to the same system (substance mixture, eluent, column).

15. Method according to claim 1, wherein the inputted data and/or results of a run are compared with the stored data, and, if the data agree within preset limits, the stored data of the best run for this system are used for the next run.

16. Device for the automatic performance and optimization of chromatographic investigations comprising:
  a) A chromatography separation column,
  b) An inlet chamber for the substance mixture,
  c) A feed apparatus for the eluent,
  d) A detection and measuring unit at the outlet of the chromatography column,
  e) A data-recording unit for the automatic and/or manual recording of data, wherein
  f) the data-recording unit is allocated an optimization unit which calculates, on the basis of the most recently recorded data of a system, optimized parameters for a chromatography run and
  g) a control apparatus and parameter sensors are provided, the control apparatus being connected to the optimization unit such that the calculated optimized parameters are automatically set by the control apparatus and an automatic chromatography run takes place with this setting.

17. Device according to claim 16, wherein for the optimization and/or decision for optimized data, the device includes a module that operates according to the principles of artificial intelligence.

18. Device for the automatic performance and optimization of chromato graphic investigations-comprising:
  a) a chromatography separation column,
  b) an inlet chamber for the substance mixture,
  c) a feed apparatus for the eluent,
  d) a detection and measuring unit at the outlet of the chromatography column,
  e) a data-recording unit for the automatic and/or manual recording of data,
  f) the data-recording unit is allocated an optimization unit which calculates, on the basis of the most recently recorded data of a system, optimized parameters for a chromatography run and
  g) a control apparatus and parameter sensors are provided, the control apparatus being connected to the optimization unit such that the calculated optimized parameters are automatically set by the control apparatus and an automatic chromatography run takes place with this setting.
wherein in the search for optimized parameters a so-called Monte Carlo optimization is carried out.

19. Device according to claim 18, wherein a module is provided which evaluates the criteria maximum number of peaks, separation of peaks and overall time limit of a parameter selection, and deduces specific parameters therefrom.

20. Device according to claim 16, wherein change apparatuses are provided for the transfer to a different column material and/or a different eluent.

* * * * *